United States Patent [19]
Helfet

[11] 4,261,064
[45] Apr. 14, 1981

[54] BICONDYLAR JOINT PROSTHESIS

[76] Inventor: Arthur J. Helfet, 1917 Trust Bank Centre, Heerengracht, Cape Town, South Africa

[21] Appl. No.: 13,408

[22] Filed: Feb. 21, 1979

[30] Foreign Application Priority Data

Feb. 17, 1978 [GB] United Kingdom ............... 06293/78

[51] Int. Cl.³ .......................... A61F 1/24; A61F 1/04; A61F 1/08
[52] U.S. Cl. ....................... 3/1.91; 3/1.911; 3/22; 128/92 C
[58] Field of Search ................. 3/1.9–1.911, 3/22; 128/92 C

[56] References Cited

U.S. PATENT DOCUMENTS

| | | | |
|---|---|---|---|
| 3,728,742 | 4/1973 | Averill et al. | 3/1.911 |
| 3,748,662 | 7/1973 | Helfet | 3/1.911 |
| 3,774,244 | 11/1973 | Walker | 3/1.911 |
| 3,869,731 | 3/1975 | Waugh et al. | 3/1.911 |

*Primary Examiner*—Ronald L. Frinks
*Attorney, Agent, or Firm*—Diller, Ramik & Wight

[57] ABSTRACT

A bicondylar joint prosthesis for articulating two portions of a natural or artificial limb including two pairs of co-acting male and female condylar components of artificial material, the male components consisting of male medial and lateral protruberances having substantially identical part-spherical articulating surfaces engageable with a respective complementary female medial and lateral condylar component, the lateral pair of condylar components being shaped to allow relative angular deflection of the two limb portions simultaneously about two axes, a first axis of the two axes lying in a medial-lateral plane of the prosthesis passing through a common mean center of relative rotation of the lateral components and a second axis of the two axes also passing through the common mean center and being substantially normal to the first axis while the medial condylar components are shaped to roll on each other about both axes, the rolling motion about the second axis producing angular deflection of the first axis in a plane substantially normal to the general axes of the limb in extension, the medial male condylar protruberance having a curvature about the first hinge axis, the co-acting female medial condylar component being constituted by a groove having a radius of curvature about the second axis, and the bottom of the groove being substantially flat or having a radius of curvature about the first hinge axis which tends to infinity and is greater than the radius of curvature about the first hinge axis of the male condylar protruberance.

8 Claims, 8 Drawing Figures

BICONDYLAR JOINT PROSTHESIS

This invention relates to bicondylar joint prosthesis or replacements (hereinafter described for convenience in relation to knee joints) and is an improvement in or modification of the invention disclosed in U.S. Pat. No. 3,748,662. In the said patent there is claimed a bicondylar joint prosthesis for articulating two portions of a natural or artificial human limb and comprising two pairs of coacting male and female condylar components of artificial material, the male components consisting of medial and lateral protuberances each engageable with a respective complementary female medial or lateral condylar component, the lateral pair of condylar components being shaped to allow relative angular deflection of the two limb portions simultaneously about two axes, the first or hinge axis passing in the medial-lateral direction through the common means centre of relative rotation of the lateral condyles and the second axis also passing through the said centre and lying in a plane substantially normal to the first or hinge axis whilst the medial condylar components are shaped to roll on each other about both axes, the rolling motion about the second axis producing angular deflection of the first or hinge axis in a plane substantially normal to the general axis of the limb in extension.

A feature of the particular embodiment described for a knee and illustrated in the specification and drawings of the said patent is that the medial tibial condyle is a groove having a radius of curvature about the first or hinge axis, as shown at $R_2$ in FIG. 4 of the drawings of the patent.

Clinical investigations of natural knee joint behaviour in groups of patients have shown that the complex motion of a natural healthy knee in flexion or extension includes a component of migration of the instantaneous centre of rotation, and in the construction of prosthesis described in the specification and drawings of the said patent this natural complex motion of the knee can be simulated more or less effectively by control of the curvature $R_2$. It is now, however, recognized that the cost of manufacture of a prosthesis having such a complex curvature of the groove constituting the tibial medial condyle is rarely justified by results in any given patient, particularly since the extent of the said migration component of natural knee motion is often difficult to determine accurately in any one patient and is liable to vary from patient to patient, and its contribution to a patient's comfort of gait is probably small compared with that resulting from the provision of the simple facility for tibial rotation resulting from the use of spherically contoured lateral condyles and a concentrically curved medial tibial condyle.

According to the present invention a bicondylar joint prosthesis is provided for articulating two portions of a natural or artificial human limb and comprises two pairs of coacting male and female condylar components of artificial material, the male components consisting of medial and lateral protuberances each engageable with a respective complementary female medial or lateral condylar component, the lateral pair of condylar components being shaped to allow relative angular deflection of the two limb portions simultaneously about two axes, the first or hinge axis passing in the medial-lateral direction through the common mean centre of relative rotation of the lateral condyles and the second axis also passing through the said centre and lying in a plane substantially normal to the first or hinge axis whilst the medial condylar components are shaped to roll on each other about both axes, the rolling motion about the second axis producing angular deflection of the first or hinge axis in a plane substantially normal to the general axis of the limb in extension characterized in that the medial male condylar protuberance has a curvature about the mean hinge axis, the co-acting female medial condylar component being constituted by a groove having a radius of curvature about said second axis, and the bottom of said groove being substantially flat or having a radius of curvature about the mean hinge axis which tends to infinity and is greater than the radius of curvature about the mean hinge axis of the male condylar protuberance. In terms of the drawings of the U.S. Pat. No. 3,748,662, this means that the centreline of the bottom of the groove 15 represented by the section line IV—IV in FIG. 3 of the said patent lies in a plane substantially normal to the axis of the tibia.

In this specification, the mean hinge axis defines the average position of the medial-lateral axis about which the motions of the joint during flexion and extension take place.

Preferably the lateral male condylar protuberance is part of a sphere or spheroid and engages a complementary female condylar socket or spherical or spheroidal shape having substantially the same radius as the male protuberance.

The contour of the groove seen in section on a plane containing the main hinge axis may be a circular arc of the same radius as that of the spherical contour of the articulating surface of the lateral female condylar.

Advantageously, the curvature of the articulating surfaces of the male medial and lateral condyles conform to spheres of the same radius which is substantially equal to that of the female lateral condyle.

A practical embodiment of the present invention will now be described, by way of example only, with reference to the accompanying drawings in which.

Figure 1:
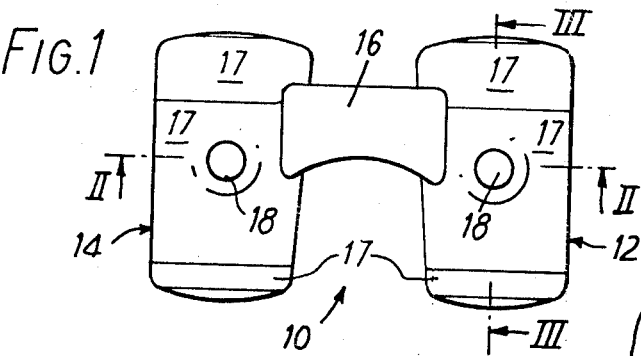
FIG. 1 is a plan view of the femoral condyles in a knee joint according to the invention.

The prosthesis illustrated in the drawings is intended as a replacement for a knee joint.

Figure 3:
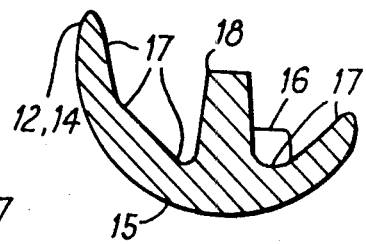
FIG. 3 is a section on the line III—III of FIG. 1.
Figure 2:
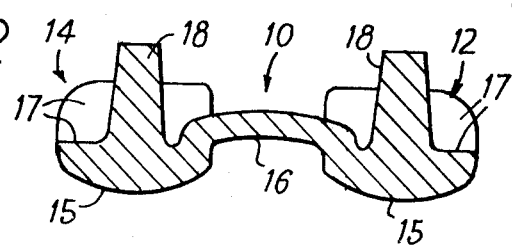
FIG. 2 is a section on the line II—II of FIG. 1.
Figure 6:
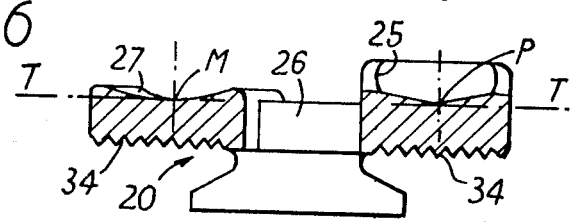
FIGS. 5-8 are sections on the lines, respectively, V—V, VI—VI, VII—VII and VIII—VIII of FIG. 4.
Figure 7:
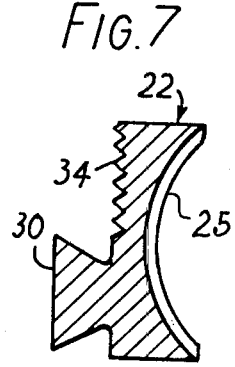
Figure 4:
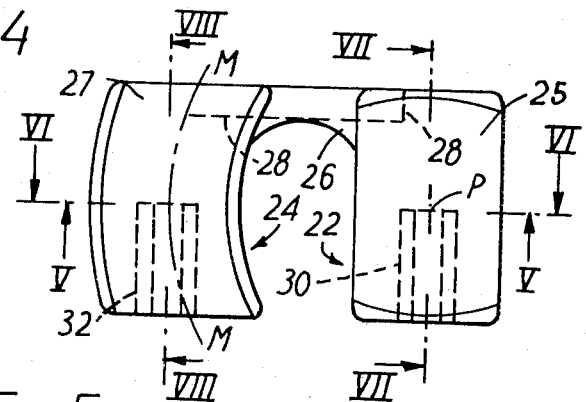
FIG. 4 is a plan view of the tibial condyles.
Figure 8:
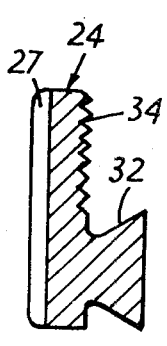
Figure 5:
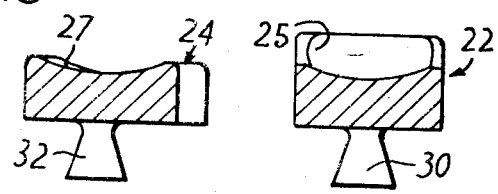

Referring first to FIGS. 1-3, the femoral implant 10 has male femoral condyles 12, 14 constituted by a pair of identically shaped and dimensioned "shoes", of approximately constant thickness, each of which has a spherically contoured bearing or articulating surface 15 (FIGS. 2 and 3). The radii of these surfaces are equal. The opposite back (upper) surface of each shoe is formed as a series of flats 17 to facilitate bedding of the implant 10 on the prepared end of the femur. The condylar shoes 12, 14 are rigidly interconnected by a frontal bridge 16 which maintains their relative alignments and spacing. Each femoral condyle 12, 14 has, on its back (upper) surface, remote from the bearing surface 15, an integral peg or post 18 which forms a fixing stem by which the implant is secured to the femur. The identity of shape and dimension of the male femoral condyles 12, 14 renders the implant suitable for fitting either to a right or to a left femur. FIGS 4-8 show the coacting implant 20 for a right tibia. This consists of a female tibial lateral condyle 22 and a female tibial medial condyle 24 which are rigidly interconnected by a frontal bridge 26. The articulating surface 25 of the lateral condyle 22 is a spherically contoured socket of the same radius as the surfaces 15 on the femoral condyles 12, 14 so that either of the latter is a snug fit therein. In a left tibial implant, the condyles 22, 24 are reversed side for side in FIGS. 4–6. The articulating surface 27 of the medial condyle 24 is an arcuate groove having a radius at its centreline M—M in the transverse plane of FIG. 4 (normal to the axis of the tibia) which is struck about the mid-point P of the lateral articulating surface 25. The contour of the groove 27 seen in cross-section on the line V—V or VI—VI in FIG. 4 (i.e. in a plane containing the axis of the tibia) is a circular arc of the same radius as the surface 15 on the femoral condyles 12, 14, whilst the curved centreline M—M lies in the transverse plane T—T (FIG. 6). In other words, the groove 27 is tangential for the full length of its bottom to a plane normal to the axis of the tibia, and the spherical lateral articulating surface is tangential to the same plant T—T at the point P, the groove thus being substantially flat or it may have a radius of curvature about the mean hinge axis which tends to infinity and is greater than the radius of curvature of the femoral condyles 12, 14.

The tibial implant has integral frontal, lateral and medial dovetail projections 28, 30, 32 respectively on its back (under) surfaces which provide fixing posts or stems for securing the implant in complementary recesses in the head of the tibia. The back or under surfaces of the condyles 22, 24 are also serrated at 34 (FIGS. 6–8) to increase the grip afforded by the conventional cement used for securing surgical implants. The whole implant can thus be very positively located on the tibia both laterally and torsionally.

If, therefore, a femoral implant 10 having the same intercondylar spacing as a tibial implant 20 is fitted thereto so that the articulating surfaces 15, 25 of the respective lateral condyles 12, 22 (assuming a right leg prosthesis) mate, the femoral medial condyle 14 fits snugly into the groove 27 of the tibial medial condyle 24 and can roll along the groove as the femoral lateral condyle 12 twists in the tibial lateral socket 25 with which it forms a ball and socket type universal joint.

When implanted into a patient's leg, and when the latter is in full extension, the frontal end of the femoral medial condyle 14 (adjacent the frontal bridge 16) rests on the frontal end of the tibial medial condyle 24 (adjacent the bridge 26). As the knee flexes, the femoral lateral condyle 12 pivots in the tibial lateral socket 25 about the common centre of their respective spherical articulating surfaces 15, 25. This centre is the point O in FIG. 1 of the drawings of U.S. Pat. No. 3,748,662. Simultaneously, the medial condyles 14, 24 roll on each other lengthwise of the arcuate groove 27, the spherical articulating surface 15 of the femoral medial condyle 14 behaving in the same way as the curved rib 24 shown in FIGS. 5–10 of the drawings in U.S. Pat. No. 3,748,662. Flexion and extension of the knee prosthesis 10, 20 takes place about the mean hinge axis which is shown at X—X in FIG. 1 of the drawings of U.S. Pat. No. 3,748,662, while the axis itself deflects angularly between the limiting positions Y—Y (full flexion) and Z—Z (fullextension) shown in FIG. 2 of those drawings. The deflection of the mean hinge axis of the prosthesis 10, 20 thus occurs in a transverse plane only, and no deflection thereof occurs in the plane of FIG. 4 of the drawings of the U.S. patent, referred to.

The present modified construction of bicondylar prosthesis has certain practical advantages.

The tibial-medial condylar groove 27 is easier to machine than the groove 15 or 25 of U.S. Pat. No. 3,748,662 since its contour is a part of the envelope generated by a fixed circular arc lying in a plane normal to that of FIG. 4 of the accompanying drawings while the tibial implant 20 is swung in the plane of the same figure about the point P. In practice, the circular arc can be the generatix of a spherical or part-spherical rotary tool held at constant height above a work-table of a machine tool to which the tibial implant 20 is firmly clamped and which can be rotated in the plane of FIG. 4 about an axis normal to that plane through the point P. Tolerances and surface finish of the groove 27 can thus be held within close limits.

The femoral condyles 12, 14 are of identical shape and dimensions thus reducing manufacturing costs. Because of this identity, only one design of femoral implant requires to be stocked for fitting to either a right or left limb, the only variable involved being the length of the bridge 16 which determines the inter-condylar spacing.

Normally the femoral implant 10 will be made of a biologically inert metal and the tibial implant 20 will be made of a high density wear resistant plastics material such as polyethylene.

What I claim is:

1. A bicondylar joint prosthesis for articulating two portions of a natural or artificial human limb comprising two pairs of co-acting male and female condylar components of artificial material, the male components consisting of male medial and lateral protruberances having substantially identical part-spherical articulating surfaces engageable with a respective complementary female medial and lateral condylar components, the lateral pair of condylar components being shaped to allow relative angular deflection of the two limb portions simultaneously about two axes, a first axis of said two axes lying in a medial-lateral plane of the prosthesis passing through a common mean centre of relative rotation of the lateral components and a second axis of said two axes also passing through said common mean centre and being substantially normal to the first axis while the medial condylar components are shaped to roll on each other about both axes, the rolling motion about the second axis producing angular deflection of the first axis in a plane substantially normal to the general axis of the limb in extension, the medial male condylar protruberance having a curvature about the first hinge axis, the co-acting female medial condylar component being constituted by a groove having a radius of curvature about said second axis, said second axis also lying approximately at the midpoint of said female lateral condylar component, and the bottom of said groove being substantially flat or having a radius of curvature about the first hinge axis which tends to infinity and is greater than the radius of curvature about the first hinge axis of the male condylar protruberance.

2. A prosthesis according to claim 1 wherein the lateral male condylar protruberance engages a complementary lateral female condylar socket of spherical or spheroid shape having substantially the same radius as the male protruberance.

3. A prosthesis as claimed in claim 2 in which the contour of cross-section of the groove taken in a plane containing the mean hinge axis is a circular arc of the same radius as that of the spherical contour of the articulating surface of the lateral female condylar.

4. A prothesis as claimed in claims 1, 2 or 3 in which the contour of the articulating surface of the male medial and lateral condyles conform to spheres of the same radius which is substantially equal to that of the female lateral condyle.

5. A prosthesis according to claim 1, 2 or 3 wherein each condyle carries a separate fixing stem.

6. A prosthesis according to claim 4 wherein the fixing stems on the tibial implant are of dovetail shape.

7. A bicondylar joint prosthesis for articulating two portions of a natural or artificial human limb comprising two pairs of co-acting male and female condylar components of artificial material, the male components consisting of male medial and lateral protruberances having substantially identical part-spherical articulating surfaces of substantially identical radii engageable with a respective complementary female medial and lateral condylar component, said female lateral condylar component having a part-spherical articulating surface defined by a radii substantially identical to the radii of said male medial and lateral articulating surfaces, the lateral pair of condylar components being shaped to allow relative angular deflection of the two limb portions simultaneously about two axes, a first axis of said two axes lying in a medial-lateral plane of the prosthesis passing through a common mean centre of relative rotation of the lateral components and a second axis of said two axes also passing through said common mean centre and being substantially normal to the first axis while the medial condylar components are shaped to roll on each other about both axes, the rolling motion about the second axis producing angular deflection of the first axis in a plane substantially normal to the general axis of the limb in extension, the medial male condylar protruberance having a curvature about the first hinge axis, the co-acting female medial condylar component being constituted by a groove having a radius of curvature about said second axis, said second axis also lying approximately at the midpoint of said female lateral condylar component, said groove being defined by a surface which at least in part lies in a plane passing through a lowermost portion of said female lateral articulating surface, and the bottom of said groove being substantially flat.

8. A bicondylar joint prosthesis for articulating two portions of a natural or artificial human limb comprising two pairs of co-acting male and female condylar components of artificial material, the male components consisting of male medial and lateral protruberances having substantially identical part-spherical articulating surfaces of substantially identical radii engageable with a respective complementary female medial and lateral condylar component, said female lateral condylar component having a part-spherical articulating surface defined by a radii substantially identical to the radii of said male medial and lateral articulating surfaces, the lateral pair of condylar components being shaped to allow relative angular deflection of the two limb portions simultaneously about two axes, a first axis of said two axes lying in a medial-lateral plane of the prosthesis passing through a common mean centre of relative rotation of the lateral components and a second axis of said two axes also passing through said common mean centre and being substantially normal to the first axis while the medial condylar components are shaped to roll on each other about both axes, the rolling motion about the second axis producing angular deflection of the first axis in a plane substantially normal to the general axis of the limb in extension, the medial male condylar protruberance having a curvature about the first hinge axis, the co-acting female medial condylar component being constituted by a groove having a radius of curvature about said second axis, said second axis also lying approximately at the midpoint of said female lateral condylar component, said groove being defined by a surface which at least in part lies in a plane passing through a lowermost portion of said female lateral articulating surface, and the bottom of said groove having a radius of curvature about the first hinge axis which tends to infinity and is greater than the radius of curvature about the first hinge axis of the male condylar protruberance.

* * * * *